(12) United States Patent
Tarunina et al.

(10) Patent No.: US 10,017,740 B2
(45) Date of Patent: Jul. 10, 2018

(54) DERIVING BROWN ADIPOSE TISSUE CELLS

(71) Applicant: PLASTICELL LIMITED, London (GB)

(72) Inventors: Marina Tarunina, Stevenage (GB); Yen Choo, Stevenage (GB); Mylvaganam Jeyakumar, Stevenage (GB); Thomas Watson, Stevenage (GB); Meritxell Rosell, Stevenage (GB); Lilian Hook, Stevenage (GB); Diana Hernandez, Stevenage (GB)

(73) Assignee: Plasticell Limited, London (GB)

( * ) Notice: Subject to any disclaimer, the term of this patent is extended or adjusted under 35 U.S.C. 154(b) by 222 days.

(21) Appl. No.: 14/664,441

(22) Filed: Mar. 20, 2015

(65) Prior Publication Data

US 2015/0191696 A1    Jul. 9, 2015

Related U.S. Application Data

(63) Continuation-in-part of application No. PCT/EP2013/069757, filed on Sep. 23, 2013.

(30) Foreign Application Priority Data

Sep. 21, 2012 (GB) .................................. 1216934.8

(51) Int. Cl.
    *C12N 5/00*    (2006.01)
    *C12N 5/077*    (2010.01)
    *A61K 35/35*    (2015.01)

(52) U.S. Cl.
    CPC ............. *C12N 5/0653* (2013.01); *A61K 35/35* (2013.01); *C12N 2500/24* (2013.01); *C12N 2500/25* (2013.01); *C12N 2501/01* (2013.01); *C12N 2501/04* (2013.01); *C12N 2501/155* (2013.01); *C12N 2501/33* (2013.01); *C12N 2502/1352* (2013.01); *C12N 2506/1384* (2013.01)

(58) Field of Classification Search
None
See application file for complete search history.

(56) References Cited

FOREIGN PATENT DOCUMENTS

JP         2010130968    6/2010
WO   WO 2009/137613    11/2009

OTHER PUBLICATIONS

Christian Elabd, et al., Human Multipotent Adipose-Derived Stem Cells Differentiate Into Functional Brown Adipocytes, Stem Cells (2009) vol. 27, No. 11, p. 2753-2760.
Didier F. Pisani, et al., Differentiation Of Human Adipose-Derived Stem Cells Into "Brite" (Brown-In-White) Adipocytes, Frontiers in Endocrinology (2011) vol. 2, Article 87, p. 1-9.
Thien T. Tran, et al., Transplantation of Adipose Tissue And Stem Cells: Role In Metabolism And Disease, National Reviews Endocrinology (2010) vol. 6, p. 195-213.
Communication pursuant to Article 94(3) EPC dated Mar. 11, 2016, which issued during prosecution of European Application No. 13 776 954.5.
International Preliminary Report on Patentability and Written Opinion of the International Searching Authority dated Mar. 24, 2015, which issued during prosecution of International Application No. PCT/EP2013/069757.

*Primary Examiner* — Blaine Lankford
(74) *Attorney, Agent, or Firm* — Duane Morris LLP; Thomas J. Kowalski; Deborah L. Lu

(57) ABSTRACT

The present invention relates to brown adipose tissue (BAT) cells derived from adult stem or progenitor cells, derived from adult white fat tissue (WAT), as well as to methods for deriving such cells.

10 Claims, 7 Drawing Sheets

DERIVING BROWN ADIPOSE TISSUE CELLS

RELATED APPLICATIONS AND INCORPORATION BY REFERENCE

This application is a continuation-n-part application of international patent application Serial No. PCT/EP2013/069757 filed 23 Sep. 2013, which published as PCT Publication No. WO 2014/044857 on 27 Mar. 2014, which claims benefit of Great Britain patent application Serial No. 1216934.8 filed 21 Sep. 2012.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to brown adipose tissue (BAT) cells, and to methods for their production. In particular, the invention relates to BAT cells which are derived from human adult stem cells, for example adipose-derived stem cells.

BACKGROUND OF THE INVENTION

Obesity is becoming a growing concern in the global population, as more is learned about the negative health effects of obesity. Severe obesity, in which a person is 50 Kg or more over ideal body weight, in particular poses significant risks for severe health problems. Accordingly, a great deal of attention is being focused on treating obese patients.

Appetite suppressing pathways have been the focal point of anti-obesity drug development, since obesity is thought to be due to excess energy intake over energy expenditure. Limiting the caloric intake, however, induces compensatory adaptations that resist weight loss, Because nutrient-sensing neurons cross talk with cognitive and behavioural components, appetite suppressants tend to produce unacceptable psychiatric side effects. However, because of the complexity of the regulation of adipogenesis, few other pathways have been explored.

Diabetes is a metabolic disorder characterised by high blood glucose levels combined with relative insulin deficiency and insulin resistance. The majority of diabetic patients suffer from type 2 diabetes also known as late onset diabetes, and the incidence of this type of diabetes has spiralled in the last few years in line with an increase in obesity.

The function of BAT is to transfer energy from food into heat; physiologically, both the heat produced and the resulting decrease in metabolic efficiency can be of significance, Heat production from brown adipose tissue is activated whenever the organism is in need of extra heat, e.g., post-natally, during entry into a febrile state, and during arousal from hibernation, and the rate of thermogenesis is centrally controlled via a pathway initiated in the hypothalamus.

BAT is abundant in rodents and human neonates but adult humans possess very little BAT and amounts decrease with aging. The amount of BAT in both rodents and humans is inversely correlated with obesity, such that rodents with defects in genes promoting BAT formation and function are prone to obesity and in humans greater amounts of BAT are observed in younger, leaner individuals than in older, over-weight subjects. Therefore methods to activate BAT tissue in obese individuals or to increase BAT mass would be expected to have a positive effect on weight loss and susceptibility to obesity associated morbidities, Accordingly, a number of proposals have been made for the introduction of BAT into adult humans to combat obesity, For example, U.S. Pat. No. 6,645,229 notes that that "brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat." Neonatal BAT and adult human BAT appear to differ in certain characteristics. For example, neonatal or classical BAT is derived from a Myf5 expressing muscle-like cellular lineage. So-called beige or brite fat comes from a different lineage, from within white adipose tissue (WAT). Recently, it has been proposed that all adult human BAT is beige/brite, rather than classical BAT (Wu et al., 2012 Cell 150:1-11)

Activating or increasing BAT mass can also have a positive effect on diseases associated with BAT—in particular diabetes (Vegiopoulos et al, 2010, Science 328 (1158-61); Seale et al 2001, JCI 121 (96-105); Bostrom et al 2012 Nature 481 (463-68), In the simplest scenario BAT can improve type II diabetes by reducing obesity and therefore WAT depots, thus reducing their induction of insulin resistance. However BAT can also improve metabolic dysfunction beyond that expected by reduction in obesity alone. This is evidenced by the fact that increased BAT improved insulin sensitivity in overweight mice even when they didn't lose weight. It has been shown that BAT can also directly influence insulin secretion from islet cells in response to glucose, improving glucose homeostasis (Guerra et al, JCI, 2001,108 (1205-1213). in addition it has recently been shown that BAT transplants in mice robustly improve the metabolic condition of obese, insulin resistant mice (Liu, et al., (2013). *Cell research*, 1-4; Stanford, et al., (2013) The Journal of clinical investigation, 123(1), 215-223), and to restore normoglycemia and glucose tolerance in streptozo-tocin-induced diabetic mice (Gunawardana & Piston, 2012 *Diabetes*, 61(3), 674-82). In addition to acting as a glucose and energy sink, brown adipocytes are likely to also secrete factors (locally and/or in the circulation) that may have beneficial effects on glucose metabolism/insulin sensitivity and overall energy balance, like IL-6 (Stanford et al., 2013).

WO2009137613 describes a method for generating BAT, on the basis of the discovery that stem cell antigen-1 positive (Sca-1+) progenitor cells treated with one or more bone morphogenic proteins (BMP) differentiate to or towards BAT cells. These BAT cells are described as genuine BAT cells with a complete capacity to respond to catecholamine stimulation by turning on the BAT cell thermogenic program.

Nishio et al, Cell Metabolism 16:394,2012, describe the generation of BAT cells from human pluripotent stem cells, The BAT generated is of the classical, rather than brite, lineage.

More recently, WO2013/123214 described the generation of human BAT from artery-derived cells by exposing internal mammary artery-derived cells (iMACs) to an adipogenic instruction medium.

Citation or identification of any document in this application is not an admission that such document is available as prior art to the present invention.

SUMMARY OF THE INVENTION

Since BAT designed for therapeutic purposes is intended to be introduced into a patient, it would be an advantage to be able to generate BAT from the patient's own tissues—i.e. to develop an autologous therapy. Therefore the use of ES cells or embryonic/foetal stem cells is not suitable despite their potential potency to generate BAT, as BAT is abundant in infants and less so in adults. Since adult adipose tissue is routinely removed by liposuction, it would be advantageous to be able to generate BAT from cells derived from WAT. Finally, since the BAT is intended to be reintroduced into a human, the use of transgenes should be avoided.

In a first aspect of the present invention, therefore, there is provided a differentiated brown adipose tissue (BAT) cell which is generated from adipose-derived adult stem cells. We have developed a protocol for the generation of BAT cells from adult WAT, starting from adipose-derived stem cells (ADSCs) present in WAT. The adult stem cells are not transgenic.

In one embodiment, the adult stem cells are adipose-derived stem (ADSCs) or progenitor cells, for example pre-adipocytes or adMSCs (adipose tissue derived mesenchymal stem cells).

In one embodiment, basal UCP1 expression is at a level at least 10 times that of white adipose tissue (WAT). UCP1 expression is a general marker for the BAT phenotype. In one embodiment, basal UCP1 expression is at least 20 times the basal UCP1 expression in WAT. UCP1 expression can be further induced by cAMP and its analogues.

In general, gene expression levels are measured in cultures of cells which have been derived from adult stem cells in accordance with the present invention. Preferably, the figures are normalised for total cell numbers, and relative comparisons therefore made between cultures of equivalent total numbers of cells. For example, expression levels can be calculated per 100 cells, or per cell, by averaging the results over the number of cells in a culture. Cell number is inferred by expression level of a housekeeping gene in the culture. Housekeeping genes are expressed at the same level in all cells. Therefore normalisation of gene expression level to the level of housekeeping gene expression in each culture allows comparison across different cultures.

In one embodiment, the BAT culture expresses PDRM16 at a basal level which is increased compared to WAT. In some examples, PDRM16 is expressed at a level about 2 times higher than the basal level in WAT.

In one embodiment, the BAT culture expresses PPARGC1a at a basal level which is increased compared to the basal expression level in WAT. For example, PPARGC1a is expressed at a level about 20 times higher than in WAT; in some examples, PPARGC1a can be expressed at a level about 40 times higher than WAT.

In one embodiment, the BAT cultures do not express CIDEA at a level increased when compared with white adipose tissue (WAT), Comparison of classical BAT genes (Eva1, FBXO31, EBF3, ZIC1) and beige specific genes (TMEM26, Tbx2, Shox2, HoxC9) suggest a beige rather than classical BAT lineage for the BAT cells of the invention, In one embodiment, CD137, which is expressed at higher levels in beige fat, is not detected in the cells of the invention.

In other embodiments, elevated basal expression of one or more of the following genes is observed compared to WAT: TBX15, FBXO31, EBF3, SHOX2, and TMEM2S.

According to a second aspect of the invention, there is provided a method for deriving a BAT cell from an adult adipose-derived stem cell, which may comprise culturing the stem cell in mesechymal stem cell growth medium, and transferring the cell to a medium which may comprise Dex, IBMX and BMP-7.

In one embodiment, the cells are not transfected with transgenes.

The method according to the present invention is extremely efficient. in one embodiment, 20% or more of the stem cells are differentiated into BAT cells, as assessed by antibody staining of cell cultures for expression of a BAT-associated gene, such as UCP-1. Preferably, 25%, 30%, 40%, 50% or more of the stem cells are differentiated into BAT.

The method, in embodiments, may comprise exposing the stem cell to the following media combinations:
(i) StemPro MSC SFM (invitrogen) and BMP-7;
(ii) DMEM/F12(w Glutamax), insulin, transferrin, BMP-7, Triidothyronine (T3), Dexamethasone, Rosiglitazone and 3-isobutyl-1-methylxanthine (IBMX); and
(iii) DMEM/F12(w Glutamax, insulin, transferrin, BMP-7, T3, Dexamethasone and Rosiglitazone.

Step (iii) above can be repeated by refreshing the medium.

Advantageously, the cells are exposed to the media sequentially, at three-day intervals. However, different timings can be determined for specific conditions, by empirical analysis.

In one embodiment, the components can be admixed as a single cocktail, and used to differentiate ADSCs in a single step procedure. This is referred to herein as a "mixed" protocol.

In another embodiment, the protocol may comprise three media combinations, as follows:
(i) StemPro MSC SFM (invitrogen);
(ii) DMEM/F12, insulin, transferrin, BMP-7, T3, Dexamethasone, Rosiglitazone and IBMX; and
(iii) DMEM/F12, insulin, transferrin, T3, Dexamethasone and Rosiglitazone.

In all media, antibiotics and/or antifungal agents can be used to prevent infection. For example, 1% penicillin/streptomycin can be used.

In a third aspect, the present invention provides a differentiated BAT cell derived by a method according to the second aspect of the invention. In embodiments, the BAT cell can be a BAT cell according to the first aspect of the invention.

In a fourth embodiment, there is provided a differentiated BAT cell according to the first embodiment, for use in treating a patient suffering from a disease characterised by excessive adipose tissue accumulation, wherein the cell is implanted into the patient.

In a fifth embodiment, there is provided a method for treating a patient suffering from a disease characterised by excessive adipose tissue accumulation, which may comprise implanting in a patient in need of said treatment one or more cells according to the first embodiment.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC, Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings.

DETAILED DESCRIPTION OF THE INVENTION

Figure 1:
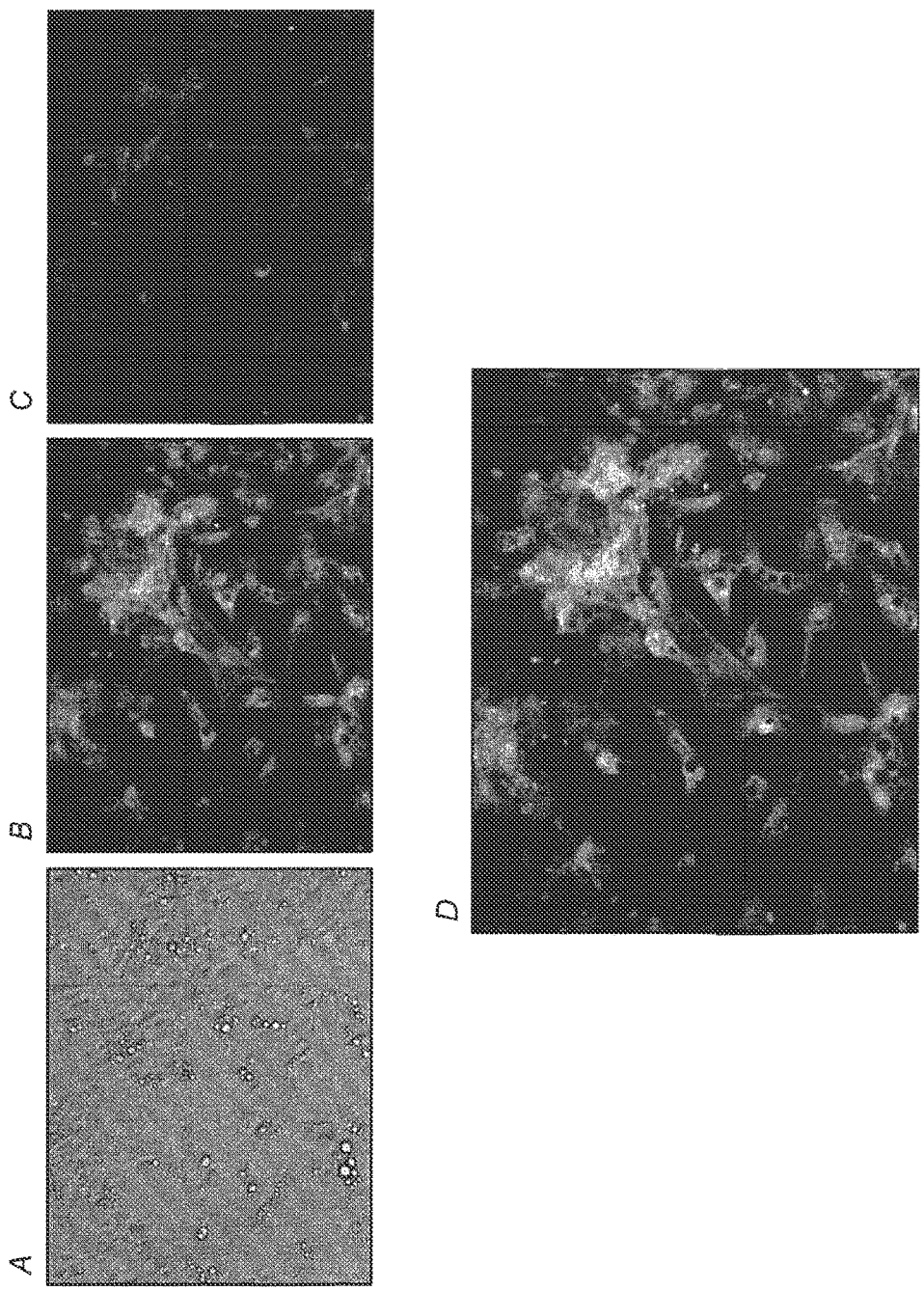
FIG. 1A-D: Example of UCP-1 and PRDM16 expression in adipose derived stern cells (Lonza), differentiated for 17 days. A) brightfield, h) staining with anti-PDMR16 Ab (Green) R&D 1:20; c) anti-UCP1 Ab (Red), SantaCruz; 1:100; d) merged PDRM16 (green), UCP-1 (red) and Hoescht (blue). ×20 magnification.

The present invention employs, unless otherwise indicated, conventional techniques of molecular biology, microbiology and recombinant DNA, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; M. J. Gait (Editor), 1984, Oligonucleotide Synthesis: A Practical Approach, Id Press; and, D. M. J, Lilley and J, E. Dahlberg, 1992, Methods of Enzymology: DNA Structure Part A: Synthesis and Physical Analysis of DNA Methods in Enzymology, Academic Press.

Definitions

Differentiated. A differentiated tissue or cell, according to the present invention, is a cell which has been derived from a unipotent, multipotent, pluripotent or totipotent cell into a cell of a defined tissue type, which in the case of the invention is brown adipose tissue or BAT.

BAT. Brown adipose tissue is tissue which has the characteristics of brown fat, preferably human brown fat, as typified by gene expression profiles associated with brown fat as described herein, or for example in Svensson et al., Int J Mol Med. 2011 February; 27(2):227-32, and which has the energy usage profile of brown fat. BAT typically expresses the UCP1 gene at levels superior to white adipose tissue, and ADSC BAT precursor cells. BAT may be of the classical or the brite (beige) lineage. The classical lineage is derived from My15 expressing cells, which are of muscle-like lineage, whereas the brite or beige lineage is derived from cells in WAT. In embodiments, the BAT cells of the present invention are of brite/beige lineage.

WAT. White adipose tissue is tissue having the characteristics of adult white fat. Preferably it is human WAT.

Cell. A cell, as referred to herein, is defined as the smallest structural unit of an organism that is capable of independent functioning, or a single-celled organism, consisting of one or more nuclei, cytoplasm, and various organelles, all surrounded by a semi-permeable cell membrane or cell wall, The starting cells from which the BAT cells according to the invention are derived are derived from adult human stem or progenitor cells, preferably stem or progenitor cells derived from adipose tissue. In an embodiment of the invention, the cells are not genetically manipulated. In one embodiment, they are mesenchymal stem cells. A stem cell is defined in more detail below, and is a totipotent, pluripotent or multipotent cell capable of giving rise to more than one differentiated cell type. Stern cells may be differentiated in vitro to give rise to differentiated cells, which may themselves be multipotent, or may be terminally differentiated. Cells differentiated in vitro are cells which have been created artificially by exposing stem cells to one or more agents which promote cell differentiation.

Adult. In the context of the present invention, a difference is drawn between embryonal, neonatal and post-neonatal tissues. Post-neonatal tissues are referred to as adult. For example, post-neonatal refers to (human) infants after one month from birth.

Transgenic. A transgenic cell, as referred to herein, is a cell which has been transfected or transformed with an exogenous gene.

Totipotent. A totipotent cell is a cell with the potential to differentiate into any type of somatic or germ cell found in the organism and extraembryonic tissue. Thus, any desired cell may be derived, by some means, from a totipotent cell.

Pluripotent. A pluripotent cell is a cell which may differentiate into all cell types of a developing embryo and adult organism but not into extraembryonic tissue.

Somatic. As used herein, the term "somatic cell" has the same meaning as is understood in the art ie. any cell forming the body of an organism other than a germ line cell. In mammals, germ line cells (also known as gametes) are the spermatozoa and ova which fuse during fertilization to produce a cell called a zygote, from which the entire mammalian embryo develops.

Culture Medium. BAT cells according to the invention can be derived by culturing adipose-derived stem cells in a culture medium, in the presence of particular agents. The medium may be a culture medium that is used for the expansion and/or passage of cells. In some instances, the composition of the culture medium will be unknown since it may comprise serum which is typically of unknown composition. In a preferred embodiment, however, each of the components of the culture medium will be known in terms of the amount or concentration thereof. In one embodiment, the culture medium may be a serum-free medium suitable for culturing stem cells, such as StemPro® MSC SFM (Invitrogen) or DMEM/F12.

Adipose-Derived Stem Cell (ADSC). As referred to herein, adipose-derived stem cells or ADSCs are stem cells derived from adipose tissue Such cells include adipose-derived mesenchymal stem cells (adMSCs), and in general other multipotent cells of adipose origin. ADSCs are available commercially from Lonza (Catalog No PT-5006) and Invitrogen (StemPro ADSC kit). adMSCs are available from PromoCell (catalog No C-12978)m ADSCs can be isolated from WAT, for example as set forth herein.

Adult Stem Cell. Any stem cell derived from an adult, as herein defined. Preferably, adult stem cells are ADSCs.

Agent. The term "agent" refers to an entity that is added (e.g. exogenously added or supplemented) to a medium in which the cell, such as an adMSC, is contained. The agent may not normally be present in the cell or the medium in which the cell is contained. The agent may be a single agent or a combination of agents—such as a combination of two or more different agents.

The present disclosure provide methods for deriving BAT cells from adult cells, and BAT cells which can be obtained by such methods. The BAT cells of the invention have particular characteristics, which are advantageous in the applications described herein.

These methods include promoting the differentiation of stem or progenitor cells to a BAT cell lineage. More specifically, the present disclosure is based, at least in part, on the discovery that stem or progenitor cells from WAT can be differentiated to produce BAT using defined conditions.

Cells

Stem cell

Stem cells are described in detail in Stem Cells: Scientific Progress and Future Research Directions Department of Health and Human Services. June 2001. http://www.nih.govlnews/stemcell/scireport.htm. Stem cells are cells that are capable of differentiating to form at least one and sometimes many specialised cell types.

To date three types of mammalian pluripotent stem cell have been isolated, or four types if induced pluripotent stem cells (iPS cells) are included. These cells can give rise to cell types that are normally derived from all three germ layers of the embryo (endoderm, mesoderm and ectoderm). The three types of stem cell are: embryonal carcinoma (EC) cells, derived from testicular tumours; embryonic stem (ES) cells, derived from the pre-implantation embryo (normally the blastocyst); and embryonic germ (EG) cells derived from the post-implantation embryo (normally cells of the foetus destined to become part of the gonads). These cells are receiving particular attention in the effort to direct differentiation, precisely because they are pluripotent. However, they are not the focus of the present invention.

Stem cells are also present in the adult organism. An adult stem cell is an undifferentiated cell that occurs in a differentiated (specialised) tissue, renews itself, and can differentiate to yield more specialised cells. They are therefore ideal for use in the present invention, as they can be obtained from the tissue of a patient and used to generate BAT. In addition to the adult stem cells there are numerous types of progenitor or precursor cells. These are cells that are partially restricted in their differentiation potential and occur in probably all of the tissues of the body-they are capable of differentiating but differ from stem cells in that their repertoire is not as broad, and by definition they are not capable of self-renewal. These cells are also useful in the context of the present invention.

Methods for obtaining samples from various tissues and methods to establish primary cell lines are well-known in the art (see for example, Jones G E, Wise C J., "Establishment, maintenance, and cloning of human dermal fibroblasts." *Methods Mol Biol.* 1997;75: 13-21). Somatic cell lines may be purchased from a number of suppliers such as, for example, the American tissue culture collection (ATCC), the German Collection of Microorganisms and Cell Cultures (DSMZ) or PromoCell GmbH, Sickingenstr. 63165, D-69126 Heidelberg.

Semi-differentiated Cell

The cell may be a progenitor cell such as multipotent progenitor cell—that can give rise to functional BAT cells. Like stem cells, progenitor cells have a capacity to differentiate into a specific type of cell type. In contrast to stem cells, however, they are already far more specific: they are pushed to differentiate into their "target" cell. The most important difference between stem cells and progenitor cells is that stem cells can replicate indefinitely, whereas progenitor cells can only divide a limited number of times. Most progenitor cells are described as unipotent or multipotent. In this point of view, they may be compared to adult stem cells. But progenitors are said to be in a farther stage of cell differentiation. They are in the "center" between stem cells and fully differentiated cell.

The kind of potency they have, depends on the type of their "parent" stem cell and also on their niche. Like stem cells, mostly, they are formed and developed in a colony, with the right conditions for them to grow and differentiate into their target tissues, Progenitor cells are found in adult organisms and they act as a repair system for the body. They replenish special cells, but also maintain the blood, skin and intestinal tissues. They can also be found in developing embryonic pancreatic tissue.

Human adipose derived stem cells can be isolated from adipose tissue by, for example, the procedure set forth in Li et al., Experimental Biology and Medicine 2012, 237:845-852, as well as US2012208274.

Cell Culture Techniques

Cell culture can be carried out by any suitable technique. The agents disclose(herein which can be used to differentiate BAT from adult stem or progenitor cells, including ADSCs or adMSCs, can be added in sequence or contemporaneously.

We have previously disclosed techniques and tools for sequential culture of cells in a variety of media, for example in EP1917349, WO2004031369, EP2491386 and EP2464720, Such techniques can be used in the context of the present invention, but are not necessary; then present application provides the conditions required to differentiate adipose precursors into BAT.

Accordingly, cell culture can be carried out in standard cell culture plates, using standard culture techniques to expose the cells to the agents described herein.

The amount (e.g., concentration or dose) of the one or more agents as well as the exposure time in cell culture will be sufficient to increase the number of BAT cells or cells with the characteristic of mature BAT cells in a population of adipocyte precursors. Both the concentration and the exposure time can be determined empirically by the skilled person.

Typically, cells are exposed to agents for a period of up to three days, for example 1 day, two days or three days. Longer incubation times may also be used.

BAT can be identified by measuring one or more BAT specific markers, such as uncoupling protein 1 (UCP1), cell death-inducing DFF45-like effector A (CIDEA), peroxisome proliferator-activated receptor gamma, coactivator 1 alpha (PGC)-1 alpha, and/or PPAR gamma coactivator (camp)-1 beta and/or PRDM-16. Alternative methods for identifying BAT include BAT morphology (e.g., using visual, e.g., microscopic, inspection of the cells); or BAT thermodynamics, e.g., cytochrome oxidase activity, measurement of Na+-K+-ATPase enzyme units, or assay of other enzymes involved in BAT thermogenesis and functional analysis after animal transplant.

Agents

Agents used in cell culture in the present invention may be formulated in any conventional manner, for example in a carrier system, for administration to the populations of cells. The carrier can be a colloidal system, such as a liposome. The carrier can also be a polymer, e.g., a biodegradable, biocompatible polymer matrix. In some embodiments, the protein can be embedded in the polymer matrix while maintaining protein integrity. The polymer may be natural, such as polypeptides, proteins or polysaccharides, or synthetic, such as poly(alpha-hydroxy) acids. Examples include carriers made of, e.g., collagen, fibronectin, elastin, cellulose acetate, cellulose nitrate, polysaccharide, fibrin, gelatine, and combinations thereof, In some embodiments, the polymer is poly-lactic acid (PLA) or co-polylactic/glycolic acid (PGLA). The polymeric matrices can be prepared and isolated in a variety of forms and sizes, including microspheres and nanospheres. Polymer formulations can lead to prolonged duration of therapeutic effect.

Generally, however, agents may be added directly to the cell culture medium, and are taken up into cells.

In some embodiments, agents may include one or more of BMP, transferrin, BMP-7, T3, Dexamethasone, Rosiglitazone and IBMX.

Derivation of BAT

BAT cells may be derived from adipose tissue stem or progenitor cells according to methods set forth herein, ADSCs for example isolated as described above, can be exposed to agents by culturing in a basic medium suitable for MSC culture.

Adipose derived stem or progenitor cells, including adMSCs, may be differentiated into BAT by an agent, or one or more agents in combination and/or in succession, As set out above, the agents may include one or more of Insulin, Transferrin, T3, Dexamethasone, BMP-7, IBMX and Rosiglitazone. The concentration of T3 used in the cell culture medium may range from 0.1 to 2 nM; the concentration of Dexamethasone may range from 1 uM to 500 nM; the concentration of IBMX can range from 100 uM 1 mM; the concentration of BMP-7 can range from 10 ng/ml 200 ng/ml;and the concentration of rosiglitazone can range between 10 nM and 1 mM. The culture medium may be any medium suitable for cell culture. Examples of culture media include LDMEM (low glucose DMEM), HDMEM (high glucose DMEM) and DMEM/F12. The culture medium may be supplemented with serum or serum proteins. Alternatively, the cells may be grown in culture medium without added serum or serum proteins. Examples of suitable media include StemPro® MSC SFM (Invitrogen) serum-free medium. Mesencult® stem cell basic medium from Stem cell Technologies, and other commercially available media for cell culture. The medium may be changed every three days for optimal differentiation. Differentiation may be monitored by a variety of methods known in the art. Changes in a parameter between a stem cell and a differentiation treated cell may indicate that the treated cell has differentiated. Microscopy may be used to directly monitor morphology of the cells during differentiation. As an example, the differentiating adipocytes may adopt the multilocular cell conformation typical of BAT adipocytes, in which fat droplets are dispersed throughout the cell cytoplasm. The cells typically also adopt a polygonal shape. Cells may be immunostained using methods well known in the art. In particular, UCP1 is a marker of BAT. For example, a primary antibody specific for UCP1 may be labelled with a fluorophore or chromophore for direct detection. Alternatively, a primary antibody may be detected with a secondary antibody that is labelled with a fluorophore, or chromophore, or is linked to an enzyme. The fluorophore may be fluorescein, FITC, rhodarnine, Texas Red, Cy-3, Cy-5, Cy-5,5. Alexa488, Alexa594, QuantumDot525, QuantumDot565, or QuantumDot653. The enzyme linked to the secondary antibody may be HRP, B-galactosidase, or luciferase. The labelled cell may be examined under a light microscope, a fluorescence microscope, or a confocal microscope. The fluorescence or absorbance of the cell or cell medium may be measured in a fluorometer spectrophotomer. Changes in gene expression may also be monitored at the level of messenger RNA (mRNA) using RT-PCR or quantitative real time FOR. Any marker for BAT may be employed. For example, UCP1 expression may be monitored. RNA may be isolated from cells using methods known in the art, and the desired gene product may be amplified using FOR conditions and parameters well known in the art. Gene products that may be amplified include uncoupling protein (UCP1), peroxisome proliferator-activated receptor gamma, coactivator 1 alpha (PGC)-1 alpha, and/or PPAR gamma coactivator (PGC)-1 beta and/or PRDM-16.

Proliferation of BAT

BAT cells can be proliferated in culture using commercially available media, such as Brown Adipocyte Maintenance Medium from Cosmo Bio Ltd. Alternatively, generally available culture media, such as DMEM, may be used to proliferate adipocytes.

Kits

The present invention provides kits for the generation of BAT cells from adipose tissue derived stem or progenitor cells. In some embodiments, the kits can include adipose-derived stem or progenitor cells; one or more agents capable of promoting the differentiation of the one or more stem or progenitor cells to a BAT cell lineage; optionally, a device for administering the cells to a subject and/or instructions for administration. The different components of the kit can be packaged in separate containers and admixed immediately before use. When more than one agent is included in a particular kit, the agents may be packaged separately and admixed separately before use, or packaged together if the components of the resulting mixture are stable when combined. In one embodiment, a kit according to the invention may comprise two or more of Dex, IBMX and BMP-7. In one embodiment, the kit may comprise two, three, four, five or six or more of the agents set forth above. BMP, insulin, transferrin, BMP-7, T3, Dexamethasone, Rosiglitazone and IBMX.

Kits may further include basal media such as StemPro SFM, DMEM/F12 and/or DMEM.

Optionally, the kit may comprise cells such as preadipocytes, adMSCs, from which BAT cells may be derived, as well as instruments, instructions and agents for extraction of adipose tissue and derivation of stem cells therefrom.

Therapeutic Applications

BAT derived by means of the present invention may be used for therapeutic purposes, for introduction or re-introduction into patients, to increase brown fat content in an individual.

Methods for delivery of adipose tissue are known in the art. Methods can include implanting BAT cells into a subject to be treated. Such methods are useful, for the treatment of obesity and insulin resistance in a patient, or for treating a disease associated with obesity, for example diabetes, cancer, neurodegeneration, and aging. Methods for implanting BAT cells are known in the art, and include using a delivery system configured to allow the introduction of cells into a subject, such as for example a syringe or other delivery device equipped with a needle. Typically, the BAT cells will be in a pharmaceutically acceptable medium or carrier, with or without a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof).

Various routes of administration and various sites of administration will be apparent to those skilled in the art, and include any site where adipocytes are present, including renal sub capsular, subcutaneous, central nervous system (including intrathecal), intravascular, intrahepatic, intrasplanchnic, intraperitoneal (including intraomental) and intramuscular sites. For example, the BAT cells can be implanted into the patient subcutaneously.

It is an advantage of the invention that the implanted cells can be derived from the patient's own cells, and will therefore be immunologically compatible. Where non-immunologically compatible cells are used, an immunosuppressive compound can be administered.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Isolation of Human AdMSCs.

Human adMSCs were isolated from subcutaneous adipose tissues obtained from young donors undergoing elective surgical procedures. Approximately 1.5 g of adipose tissues were washed with phosphate-buffered saline (PBS) and finely minced, and were then digested with 0.15% collagenase type I (Sigma, St Louis, Mo., USA) at 37° C. for 30 min in a water-bath shaker (200 rpm). The collagenase was inactivated by the addition of Dulbecco's modified Eagle's medium (DMEM) supplemented with 10% fetal calf serum, penicillin (50 U/mL) and streptoymcin (50 mg/mL). The adMSC containing cell suspension was centrifuged at 600 g for five minutes. The isolated cells were plated in 25 cm$^2$ cell culture flasks at a density of $2.5 \times 10^4$ cells and cultured in standard culture medium at 378C with 5% CO2. Cultures were washed with PBS after 48 h to remove unattached cells, and re-fed with fresh medium. adMSCs were expanded up and were characterized by adipogenic differentiation. Adipogenic differentiation of ADMSCs using an adipogenesis kit (Cyagen Biosciences) was confirmed by Oil Red O (Sigma) staining of lipid droplets after 14 days of culture (FIG. 14 Culture media with different pH levels were prepared by adding an appropriate amount of sterilized HCl (1 mol/L) and NaOH (1 moll) into DMEM and monitoring using a commercial pH microelectrode (Lazarlab, Los Angeles, Calif., USA) (sensitive to 0.01 pH unit). Media with four pH levels, including 7.4 (standard condition), 7.1 (normal IVD), 6.8 (mildly degenerated IVD) and 6.5 (severely degenerated IVD) were obtained. The culture media were kept at 37° C. with 5% $CO_2$ for three days to allow pH equilibrium (CO2-dependent). adMSCs in passage 2 were cultured either in 24-well plates for cell proliferation assay or in 25 cm$^2$ cell culture flasks for cell viability and gene and protein expression analysis. The cells were re-fed with fresh medium on day 3 and harvested for analysis on day 6.

Example 2

Differentiation of BAT

Adipose derived stem cells are seeded at 30,000 cells/cm$^2$(day 0) in standard growth medium (StemPro SFM, Invitrogen). Three days later and at subsequent days indicated below the following medium formulations are added to the cells. Cell culture components are commercially available, BMP7 is bone morphogenetic protein 7b. Culture media may comprise penicillin and streptomycin (1%) to prevent infection.

TABLE 1

| | Day | | | | |
|---|---|---|---|---|---|
| | 3 | 6 | 9 | 12 | 15 |
| Basal Media | StemProSFM | DMEM/F12 | DMEM/F12 | DMEM/F12 | DMEM/F12 |
| | | Insulin (5 µg/ml) | Insulin (5 µg/ml) | Insulin (5 µg/ml) | Insulin (5 µg/ml) |
| | | Transferrin (10 µg/ml) | Transferrin (10 µg/ml) | Transferrin (10 µg/ml) | Transferrin (10 µg/ml) |
| Components | BMP7 | BMP7 (50 ng/ml) | BMP7 (50 ng/ml) | BMP7 (50 ng/ml) | BMP7 (50 ng/ml) |
| | | T3 (0.5 nM) | T3 (0.5 nM) | T3 (0.5 nM) | T3 (0.5 nM) |
| | | Dexamethasone (2 µM) | Dexamethasone (200 nM) | Dexamethasone (200 nM) | Dexamethasone (200 nM) |
| | | Rosiglitazone (100 nM) | Rosiglitazone (100 nM) | Rosiglitazone (100 nM) | Rosiglitazone (100 nM) |
| | | IBMX (250 µM) | | | |

Cells are fixed at day 17 and analysed for BAT gene expression and morphology.

Results

Figure 2:
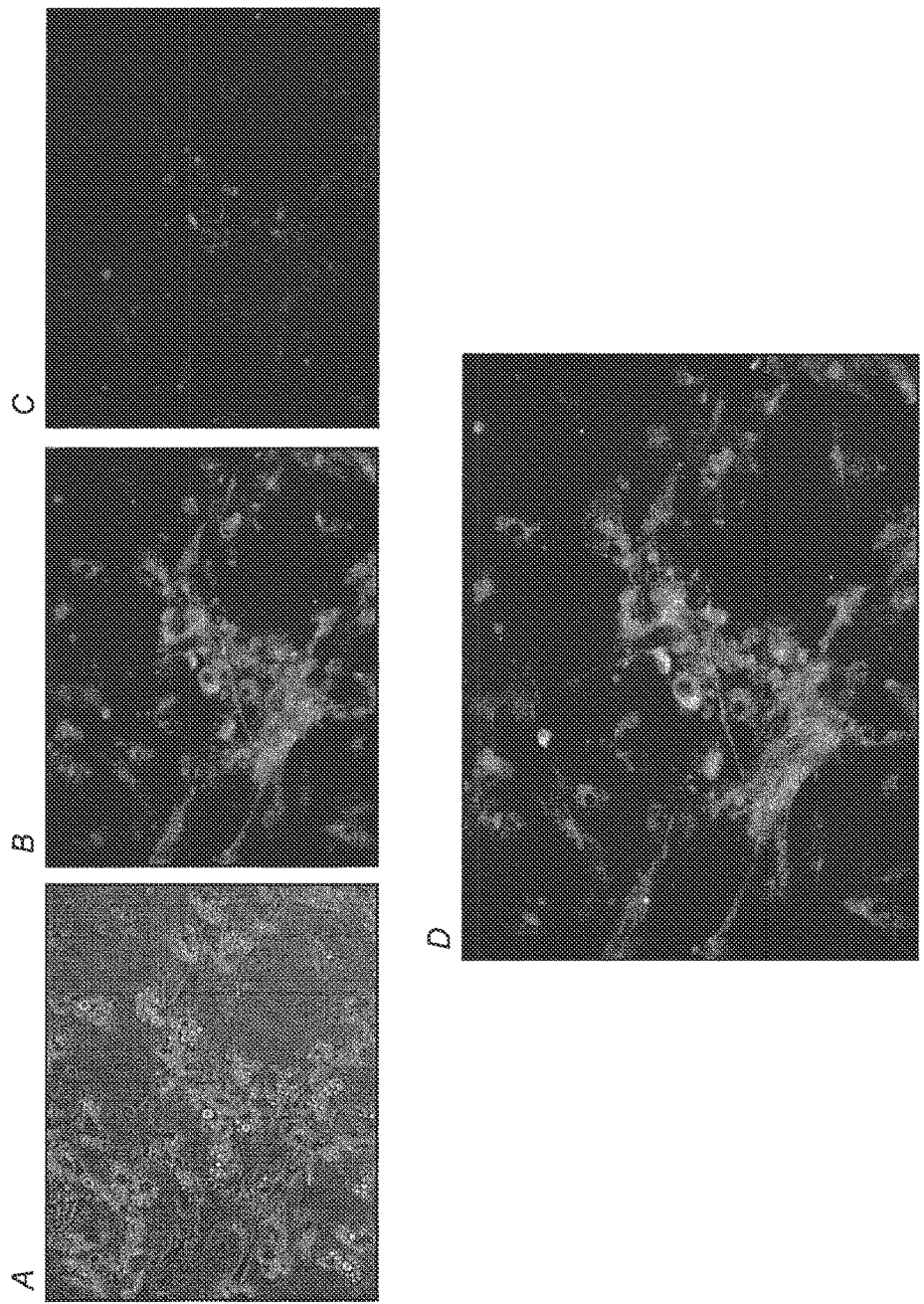
FIG. 2A-D: $2^{nd}$ example of UCP-1 and PRDM16 expression in adipose derived stem cells (Lonza), differentiated for 17 days. A) brightfield, b) staining with anti-PDMR16 Ab (Green) R&D 1:20; c) anti-UCP1 Ab (Red), SantaCruz; 1:100; d) merged PDRM16 (green), UCP-1 (red) and Hoescht (blue). ×20 magnification.

FIGS. 1 and 2 show UCP1 and PRMD1 expression in cells derived from ADSCs (Lonza). The cells show all of the characteristics of BAT.

Figure 3:
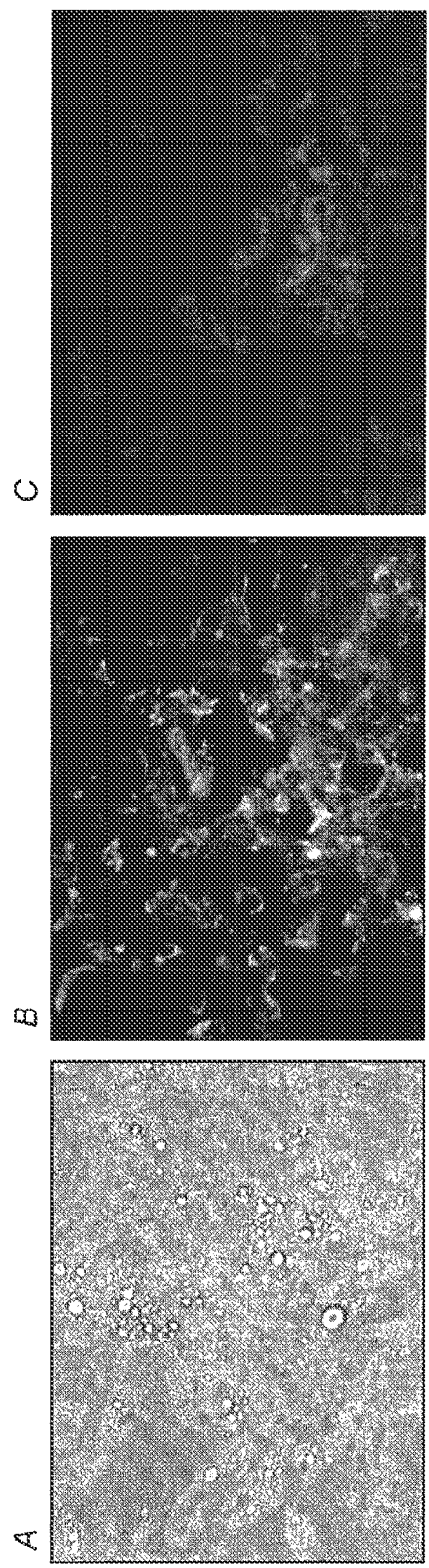
FIG. 3A-C: Example of UCP-1 and cytochrome C oxidase expression in adipose derived stem cells (Lonza), differentiated for 17 days. A) brightfield, b) staining with anti-UCP-1 Ab (Green); SantaCruz; 1:100 c) anti-Cyt C Ab (Red), invitrogen; 1:100). ×10 magnification.

FIG. 3 shows the results of UCP1 and Cytochrome C oxidase staining on cells derived as set forth above. Again, the cells show characteristics BAT.

Figure 4:
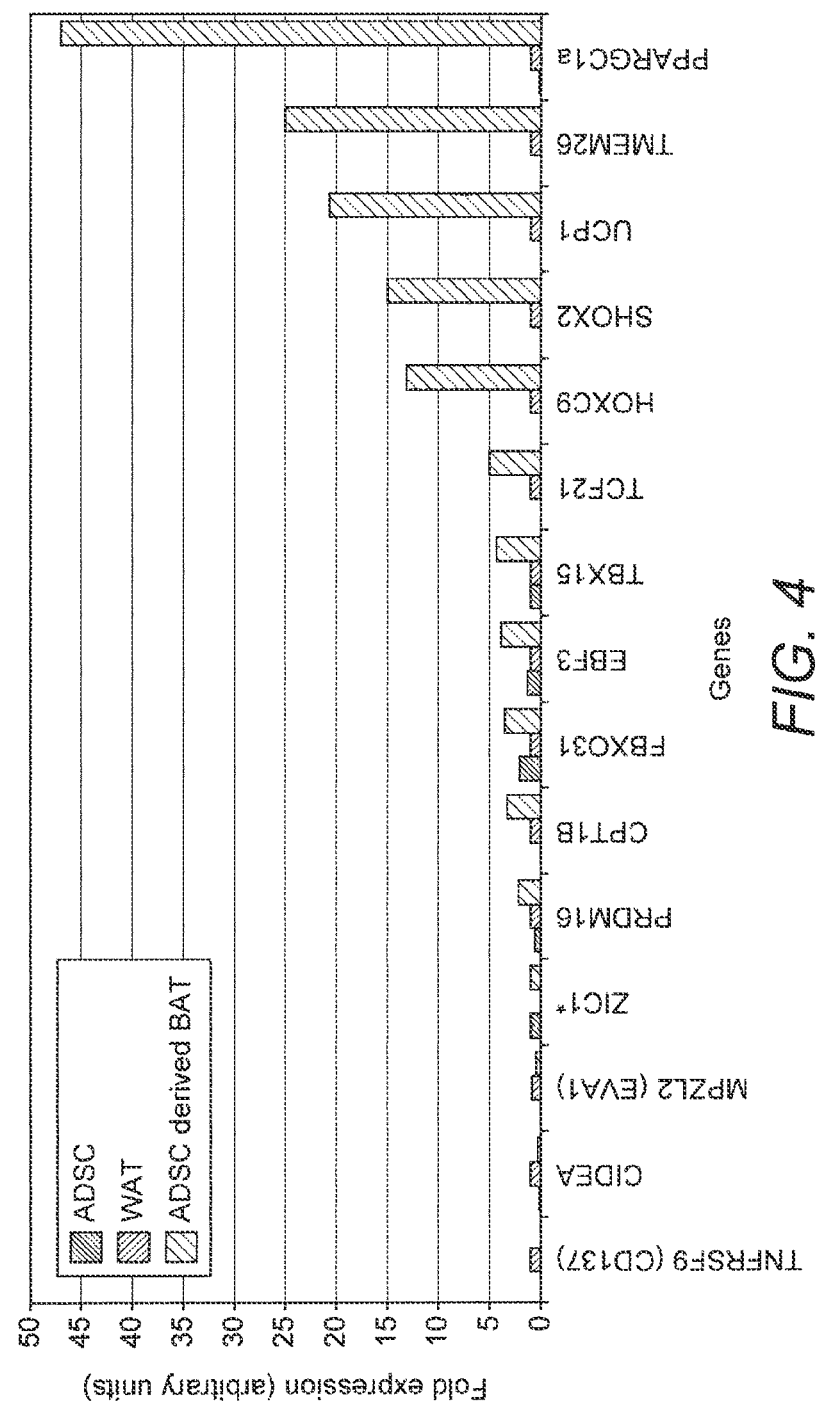
FIG. 4: qPCR analysis of gene expression in adipose derived stem cells (Invitrogen), differentiated for 17 days. Expression levels in ADSCs and differentiated BAT cells are relative to expression in white adipose tissue which is set at 1 for each gene.

FIG. 4 shows the results of qPCR gene expression analysis from the BAT cells derived as described above, These results confirm the presence of a BAT phenotype, interestingly, CIDEA is not overexpressed compared to WAT, The genes expressed in the BAT cells derived according to the invention, and their associated lineages, are set forth in Table 2 below:

| Gene | Tissue |
|---|---|
| UCP1 | All BAT |
| PRDM16 | All BAT |
| TBX15 | BEIGE |
| CIDEA | All BAT |
| PPARGC1a | All BAT |
| TCF21 | WHITE |
| FBXO31 | Classical BAT |
| EBF3 | Classical BAT |
| ZIC1* | Classical BAT |
| SHOX2 | BEIGE |
| HOXC9 | BEIGE |
| CPT1B | Classical BAT |
| TMEM26 | BEIGE |
| MPZL2 (EVA1) | Classical BAT |
| TNFRSF9 (CD137) | BEIGE |

Example 3

Single Step Protocol

The procedure outlined in Example 1 was repeated, replacing the serial culture protocol with a single-step ("mixed") protocol. In this experiment, ADSCs were incubated in MSC SFM medium, and then transferred directly into differentiation medium for the duration of the differentiation period (15 to 16 days).

| | Day | | |
|---|---|---|---|
| | 0 | 2 | 2-15 |
| Basal Media | StemProSFM | DMEM/F12 1 × ITSE | Medium refreshed every 2-3 days |
| Components | | BMP7 (50 ng/ml) | |
| | | T3 (1 nM) | |
| | | Dexamethasone (µM) | |
| | | Rosiglitazone (100 nM) | |
| | | IBMX (250 µM) | |

ITSE is a cell commercially available cell culture medium supplement containing transferrin and insulin; the remaining components are identical to the reagents used in Example 2.

Results are set forth in FIGS. 5 to 8, which are further described in Example 4.

Example 4

Differentiation of BAT Using Second Protocol

Adipose derived stem cells are seeded 50,000 cells/cm$^2$ (day 0) in StemPro SFM (Invitrogen) 2 days later media are replaced by differentiation media according to the following formulations, again containing 1% penicillin and streptomycin, After day 6, media are refreshed every 2-3 days until day 14 or 15 of differentiation.

| | Day | | | | |
|---|---|---|---|---|---|
| | 0 | 2 | 3 | 6 | 6-15 |
| Basal Media | StemPro SFM | DMEM/F12 Insulin (5 µg/ml) Transferrin (10 µg/ml) | Media and components as in day 2 refreshed | DMEM/F12 Insulin (100 ng/ml) Transferrin (10 µg/ml) | Media and components refreshed every 2-3 days as in day 6 |

-continued

| | Day | | | | |
|---|---|---|---|---|---|
| | 0 | 2 | 3 | 6 | 6-15 |
| Components | BMP7 (50 ng/ml) T3 (2 nM) Dexamethasone (200 nM) Rosiglitazone (5 μM) BMX (250 μM) | | | T3 (2 nM) Dexamethasone (30 nM) Rosiglitazone(100 nM) | |

Figure 5:
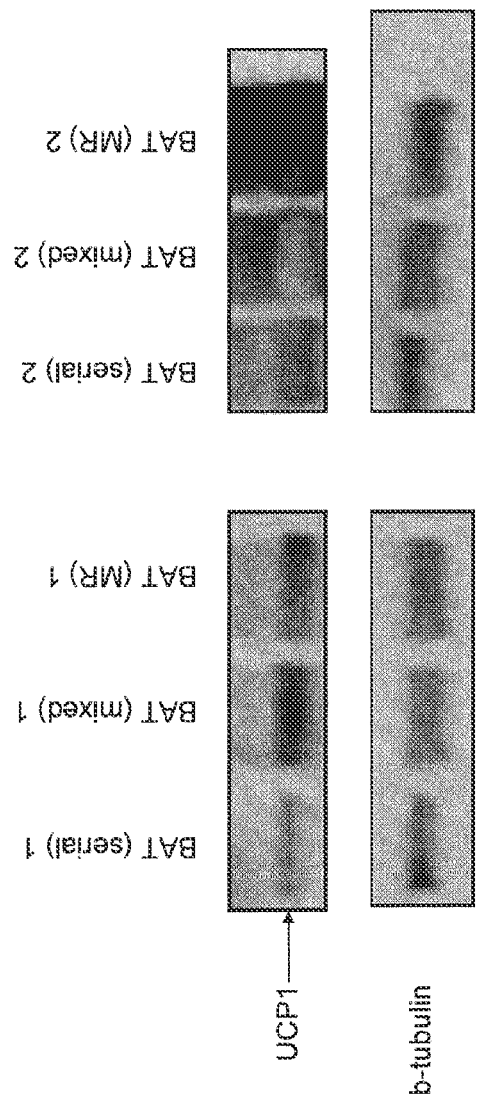
FIG. 5: Western blot analysis of UCP1 protein expression by cells obtained by the protocols of Examples 2, 3 and 4.

In order to monitor the generation of BAT, cells were analysed for the expression of various genes associated with the BAT cell type. FIG. 5 illustrates a western blot of UCP-1 expression from tissues isolated according to the protocols of Examples 2, 3 and 4. The protocol of the present Example 4 is referred to as "MR".

Figure 6:
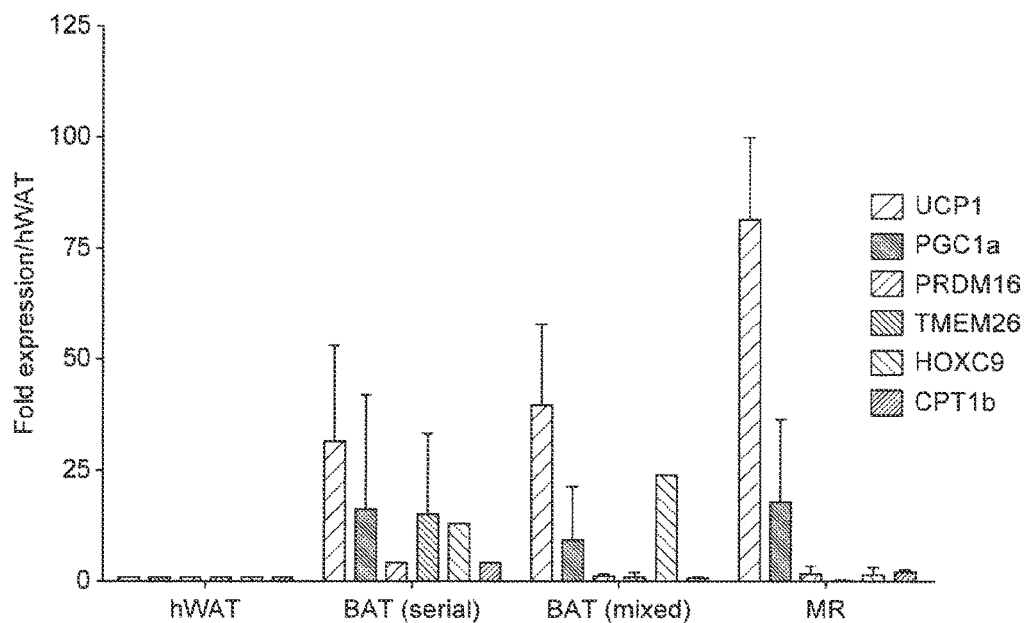
FIG. 6: Chart illustrating qPCR gene expression analysis from the BAT cells derived as described in Examples 2, 3 and 4.

FIG. 6 shows the changes in gene expression obtained with the three protocols, assessed by qPCR. in each case. UCP-1 expression is increased significantly as the cells are differentiated into BAT. The increase in expression of other markers varies according to the protocol used.

Figure 7:
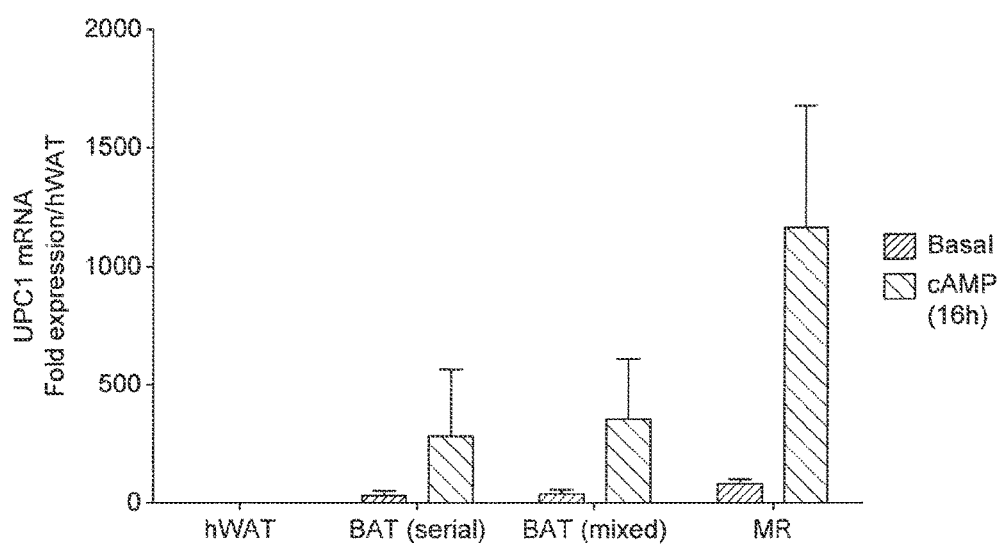
FIG. 7: qPCR UCP1 gene expression analysis from the BAT cells derived as described in Examples 2, 3 and 4, treated with the adrenergic signalling cascade second messenger cAMP, BAT activity is increased by adrenergic activation (catecholamines), Adrenergic agonists or second messengers (cAMP) potently activate UCP1 expression.

UCP-1 expression in BAT is typically cAMP inducible. The induction of UCP-1 was therefore analysed in the cells obtained by the three protocols, when induced with cAMP. The results are shown in FIG. 7. All three protocols lead the generation of cells which show cAMP-inducible gene expression, with the MR protocol giving the greatest degree of inducibility.

Figure 8A:
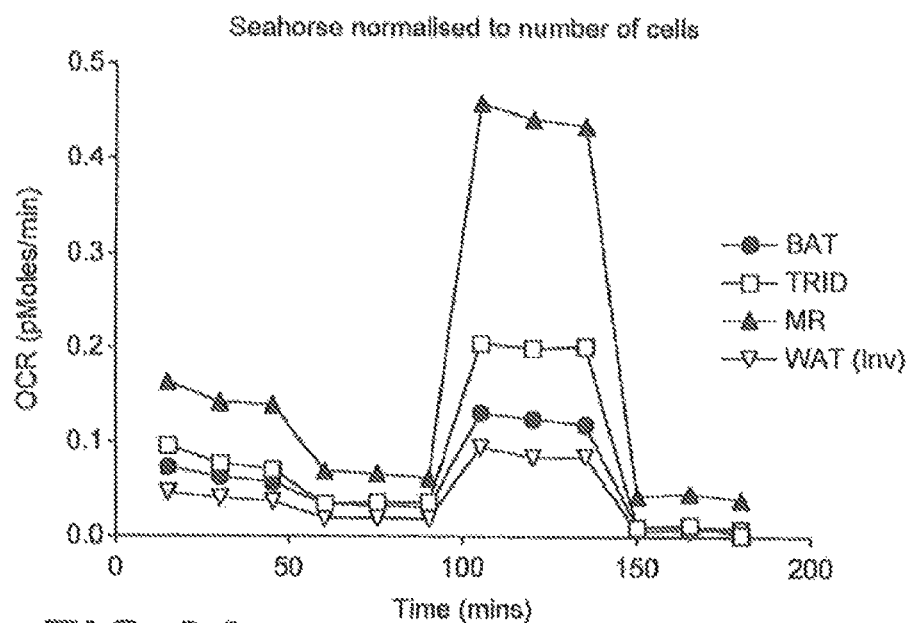
FIGS. 8A and 8B: Oxygen consumption analysis measured with the XF Cell Milo Stress Test Kit (Seahorse Bioscience) showing that cells differentiated with the BAT protocols show higher respiratory capacity when compared to cells differentiated with a published WAT protocol.
Figure 8B:
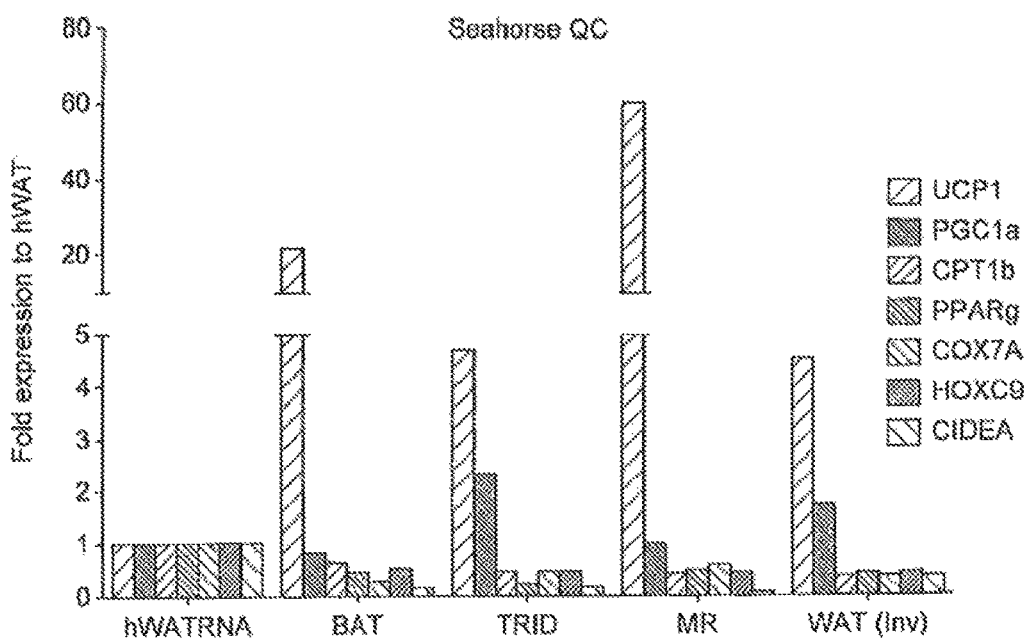

A final assay for characteristics of BAT cells involved analysis of the oxygen consumption of the cells, compared with naturally-obtained BAT. Brown adipocytes have higher mitochondrial content and express higher levels of UCP1) than white adipocytes. UCP1protein uncouples ATP production from the oxidative phosphorylation by allowing H+ to flow across the inner mitochondrial membrane producing heat and thus BAT cells shows a higher respiratory rate than white adipocytes. One of the best ways to assess respiratory capacity is by directly measuring oxygen consumption in intact cells. For that reason the Seahorse technology was used. The XF Cell Mito Stress Test Kit from Seahorse Biosciences (North Billerica, Mass.) was used to measure the four key parameters of mitochondrial function in a microplate: basal respiration. ATP turnover, proton leak, and maximal respiration. All these parameters are usually higher in BAT cells when compared to WAT cells due to, as mentioned before, higher number of mitochondria and higher expression of UCP1 protein Ahfeldt et al., (2012), Nat Cell Biol, 14(2), 209-219). The results are shown in FIGS. 8A and 8B.

Unless otherwise stated, all technical and scientific terms used herein have the same meanings as commonly understood by one of ordinary skill in the art to which this invention belongs, Any methods and materials similar or equivalent to those described herein can be used in the practice or testing of the present invention. Methods, devices, and materials suitable for such uses are described above. All publications cited herein are incorporated herein by reference in their entirety for the purpose of describing and disclosing the methodologies, reagents, and tools reported in the publications that might be used in connection with the invention.

The invention is further described by the following numbered paragraphs:

1. A differentiated brown adipose tissue (BAT) cell which is derived from adult stem cells.

2. A differentiated BAT cell according to paragraph 1, wherein the adult stem cells are not transgenic.

3. A culture of differentiated BAT cells according to paragraph 1 or paragraph 2, which culture is derived from adult stem cells.

4. A culture of differentiated BAT cells according to paragraph 3, wherein basal UCP1 expression is at a level at least 10 times that of white adipose tissue (WAT).

5. A culture of differentiated BAT cells according to paragraph 4, wherein basal UCP1 expression is at least 20 times the basal UCP1 expression in WAT.

6. A culture of differentiated BAT cells according to paragraph 3, which expresses PDRM16 at a basal level which is increased compared to WAT.

7. A culture of differentiated BAT cells according to paragraph 6, wherein PDRM16 is expressed at a level 2 times higher than the basal level in WAT.

8. A culture of differentiated BAT cells according to paragraph 3, which expresses PPRCG1a at a basal level which is increased compared to the basal expression level in WAT.

9. A culture of differentiated BAT cells according to paragraph 8, wherein PPRCG1a is expressed at a level at least 20 times higher than in WAT.

10. A culture of differentiated BAT cells according to paragraph 3, which does not express CIDEA at a level increased when compared with white adipose tissue (WAT).

11. A differentiated BAT cell or a culture of differentiated BAT cells according to any preceding paragraph, in which elevated basal expression of one or more of the following genes is observed compared to WAT: TBX15, FBXO31, EBF3, SHOX2, and TMEM26.

12, A differentiated BAT cell or a culture of differentiated BAT cells according to any preceding paragraph, which shows characteristics of a brite cell lineage.

13. A differentiated BAT cell or a culture of differentiated BAT cells according to any preceding paragraph, wherein the adult stem cell is an adipose-derived stem cell (ADSC).

14. A differentiated BAT cell or a culture of differentiated BAT cells according to paragraph 13, wherein the adult adipose-derived stem cell is an adMSC and/or a preadipocyte.

15. A differentiated BAT cell or a culture of differentiated BAT cells according to paragraph 13 or paragraph 14, wherein the adult adipose-derived stem cell is derived from WAT.

16. A method for deriving a BAT cell from an adult stem cell, comprising culturing the stem cell in mesechymal stem cell growth medium, and transferring the cell to a medium comprising Dexamethasone, IBMX and BMP-7.

17. A method according to paragraph 16, in which the cells are not transfected with transgenes.

18. A method according to paragraph 16 or paragraph 17, wherein 20% or more of the adult stem cells are differentiated into BAT cells.

19. A method according to paragraph 18, wherein 50% or more of the adult stem cells are differentiated into BAT cells.

20. A method according to any one of paragraphs 16 to 19, comprising exposing the stem cell to the following media combinations:
(i) MSC SFM and BMP-7;
(ii) DMEM/F12, insulin, transferrin, BMP-7, T3, Dexamethasone, Rosiglitazone and IBMX; and
(iii) DMEM/F12, insulin, transferrin, BMP-7,T3. Dexamethasone and Rosiglitazone.

21. A method according to paragraph 20, wherein step (hi) is repeated by refreshing the medium.

22. A method according to any one of paragraphs 16 to 21, wherein the cells are exposed to the media sequentially, at three-day intervals.

23. A method according to any one of paragraphs 16 to 21, wherein the cells are exposed to the media contemporaneously, 24. A method according to any one of paragraphs 16 to 19, comprising exposing the stem cell to the following media combinations:
(i) MSC SFM;
(ii) DMEM/F12, insulin, transferrin, BMP-7,T3. Dexamethasone, Rosiglitazone and IBMX; and
(iii) DMEM/F12, transferrin, T3, Dexamethasone and Rosiglitazone.

25. A method according to paragraph 24, wherein steps (ii) and (iii) are repeated by refreshing the medium.

26. A differentiated BAT cell or cell culture derived by a method according to any one of paragraphs 16 to 25.

27. A differentiated BAT cell or cell culture according to any one of paragraphs 1 to 15, derived by a method according to any one of paragraphs 16 to 25.

28. A differentiated BAT cell or cell culture according to any one of paragraphs 1 to 15 for use in treating a patient suffering from a disease characterised by excessive adipose tissue accumulation, wherein the cell is implanted into the patient.

29. A method for treating a patient suffering from a disease characterised by excessive adipose tissue accumulation, comprising implanting in a patient in need of said treatment one or more cells according to any one of paragraphs 1 to 15.

30. A method according to paragraph 29, wherein the disease is diabetes.

31. A kit for deriving a BAT cell from an adult stem cell, comprising two or more of the agents set forth in paragraph 20 or paragraph 23.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method for deriving a brown adipose tissue (BAT) cell from an adult adipose tissue derived stem cell, comprising culturing the stem cell in mesechymal stem cell growth medium, and transferring the cell to a medium comprising Rosiglitazone, Triiodothyronine (T3), Dexamethasone, IBMX and BMP-7.

2. A method according to claim 1, in which the cells are not transfected with transgenes.

3. A method according to claim 1, wherein 20% or more of the adult stem cells are differentiated into BAT cells.

4. A method according to claim 3, wherein 50% or more of the adult stem cells are differentiated into BAT cells.

5. A method according to claim 1, comprising exposing the stem cell to the following media combinations:
(i) MSC SFM;
(ii) DMEM/F12, insulin, transferrin, BMP-7, T3, Dexamethasone, Rosiglitazone and IBMX; and optionally;
(iii) DMEM/F12, insulin, transferrin, BMP-7, T3, Dexamethasone and Rosiglitazone.

6. A method according to claim 5, wherein step (iii) is repeated by refreshing the medium.

7. A method according to claim 1, wherein the cells are exposed to the media sequentially, at three-day intervals.

8. A method according to claim 1, wherein the cells are exposed to the media contemporaneously.

9. A method according to claim 1, comprising exposing the stem cell to the following media combinations:
(i) MSC SFM;
(ii) DMEM/F12, insulin, transferrin, BMP-7, T3, Dexamethasone, Rosiglitazone and IBMX; and
(iii) DMEM/F12, insulin, transferrin, T3, Dexamethasone and Rosiglitazone.

10. A method according to claim 9, wherein steps (ii) and (iii) are repeated by refreshing the medium.

* * * * *

UNITED STATES PATENT AND TRADEMARK OFFICE
CERTIFICATE OF CORRECTION

PATENT NO. : 10,017,740 B2
APPLICATION NO. : 14/664441
DATED : July 10, 2018
INVENTOR(S) : Marina Tarunina et al.

Page 1 of 1

It is certified that error appears in the above-identified patent and that said Letters Patent is hereby corrected as shown below:

On the Title Page

Please correct item (71) as follows:
(71) Applicant: PLASTICELL LIMITED, Stevenage (GB)

Signed and Sealed this
Seventh Day of May, 2019

Andrei Iancu
*Director of the United States Patent and Trademark Office*